(12) United States Patent
Papadopoulos

(10) Patent No.: US 9,391,216 B2
(45) Date of Patent: Jul. 12, 2016

(54) OPTICAL COUPLED SENSORS FOR HARSH ENVIRONMENTS

(75) Inventor: George Papadopoulos, Nesconset, NY (US)

(73) Assignee: Orbital ATK, Inc., Plymouth, MN (US)

(*) Notice: Subject to any disclaimer, the term of this patent is extended or adjusted under 35 U.S.C. 154(b) by 1178 days.

(21) Appl. No.: 12/479,251

(22) Filed: Jun. 5, 2009

(65) Prior Publication Data

US 2009/0302242 A1 Dec. 10, 2009

Related U.S. Application Data

(60) Provisional application No. 61/059,307, filed on Jun. 6, 2008.

(51) Int. Cl.

| H01L 31/14 | (2006.01) |
|---|---|
| G02B 27/42 | (2006.01) |
| H01L 31/0203 | (2014.01) |
| G01F 1/66 | (2006.01) |
| H01L 31/0232 | (2014.01) |
| G01N 11/00 | (2006.01) |

(52) U.S. Cl.
CPC .......... *H01L 31/0203* (2013.01); *G01F 1/661* (2013.01); *H01L 31/02325* (2013.01); *G01N 2011/008* (2013.01)

(58) Field of Classification Search
CPC ............. H01L 31/02325; H01L 31/0203; G01N 2011/006; G01N 2011/008; G01N 11/02; G01J 2009/02345
USPC ............ 250/550, 552, 208.2, 227.14, 227.19, 250/573; 356/450; 73/777, 802, 862, 73/862.324
See application file for complete search history.

(56) References Cited

U.S. PATENT DOCUMENTS

| 3,623,361 | A | * | 11/1971 | Funk, Jr. ................. 73/147 |
|---|---|---|---|---|
| 4,047,022 | A | * | 9/1977 | Holle .................. 250/201.7 |
| 4,282,510 | A | * | 8/1981 | Southgate ............. 382/279 |
| 4,339,661 | A | * | 7/1982 | Pitt et al. ............. 250/227.19 |
| 4,620,093 | A | * | 10/1986 | Barkhoudarian et al. ............. 250/231.19 |
| 4,683,760 | A | * | 8/1987 | Misumi ............... 73/861.22 |
| 4,863,270 | A | * | 9/1989 | Spillman, Jr. ........... 356/477 |
| 4,884,450 | A | * | 12/1989 | Greenwood et al. ....... 73/702 |
| 4,896,098 | A | * | 1/1990 | Haritonidis et al. ....... 324/663 |
| 5,052,228 | A | * | 10/1991 | Haritonidis .............. 73/705 |
| 5,202,939 | A | * | 4/1993 | Belleville et al. .......... 385/12 |
| 5,260,567 | A | * | 11/1993 | Kuroda et al. ........ 250/227.19 |
| 5,369,485 | A | * | 11/1994 | Hofler et al. ............. 356/477 |
| 5,381,229 | A | * | 1/1995 | Murphy et al. ........... 356/477 |
| 5,451,772 | A | * | 9/1995 | Narendran ........... 250/227.19 |
| 5,606,137 | A | * | 2/1997 | Penketh ............... 73/862.324 |
| 5,623,096 | A | * | 4/1997 | Bandyopadhyay .......... 73/147 |
| 5,633,960 | A | * | 5/1997 | Lagakos et al. ............ 385/12 |
| 5,896,191 | A | * | 4/1999 | Beier et al. ............. 356/35.5 |
| 5,945,665 | A | * | 8/1999 | Hay .................. 250/227.14 |
| 6,253,126 | B1 | * | 6/2001 | Palmer .................. 701/14 |
| 6,341,526 | B1 | * | 1/2002 | Castracane et al. ......... 73/705 |

(Continued)

*Primary Examiner* — John Lee
(74) *Attorney, Agent, or Firm* — Vidas, Arrett & Steinkraus

(57) ABSTRACT

An optical sensor comprising a light source; a sensor substrate, arranged to receive a force to be detected, the sensor substrate including an interference pattern generator, optically coupled to the light source for receiving light from the light source, and generating an interference pattern, and a detector, optically coupled to the sensor substrate for receiving the interference pattern and providing a signal which can be used to determine the force applied to the sensor substrate.

1 Claim, 9 Drawing Sheets

(56) References Cited

U.S. PATENT DOCUMENTS

| | | | |
|---|---|---|---|
| 6,341,532 B1 * | 1/2002 | Xu et al. | 73/841 |
| 6,498,681 B2 * | 12/2002 | Kartalopoulos | 359/566 |
| 6,935,193 B2 * | 8/2005 | Heisenberg et al. | 73/862.324 |
| 7,116,430 B2 * | 10/2006 | Degertekin et al. | 356/505 |
| 7,173,713 B2 * | 2/2007 | Xu et al. | 356/480 |
| 7,189,958 B2 * | 3/2007 | Spillman et al. | 250/227.14 |
| 7,196,317 B1 * | 3/2007 | Meissner et al. | 250/227.14 |
| 7,303,331 B2 * | 12/2007 | Heyworth | 374/141 |
| 7,440,117 B2 * | 10/2008 | Degertekin et al. | 356/521 |
| 7,485,847 B2 * | 2/2009 | Degertekin et al. | 250/237 G |
| 7,518,737 B2 * | 4/2009 | Hall et al. | 356/521 |
| 7,835,598 B2 * | 11/2010 | Lopushansky et al. | 385/12 |
| 2003/0145663 A1 * | 8/2003 | Heisenberg et al. | 73/862.324 |
| 2004/0130728 A1 * | 7/2004 | Degertekin et al. | 356/505 |
| 2005/0175273 A1 * | 8/2005 | Iida et al. | 385/15 |
| 2006/0181712 A1 * | 8/2006 | Degertekin et al. | 356/505 |
| 2006/0192976 A1 * | 8/2006 | Hall et al. | 356/505 |
| 2006/0227845 A1 * | 10/2006 | Degertekin et al. | 372/102 |
| 2006/0261295 A1 * | 11/2006 | Barea | 250/573 |
| 2007/0223000 A1 * | 9/2007 | Gahan et al. | 356/454 |
| 2008/0192803 A1 * | 8/2008 | Riza et al. | 374/161 |
| 2008/0297808 A1 * | 12/2008 | Riza et al. | 356/503 |
| 2009/0302242 A1 * | 12/2009 | Papadopoulos | 250/550 |
| 2010/0128284 A1 * | 5/2010 | Riza et al. | 356/519 |

* cited by examiner

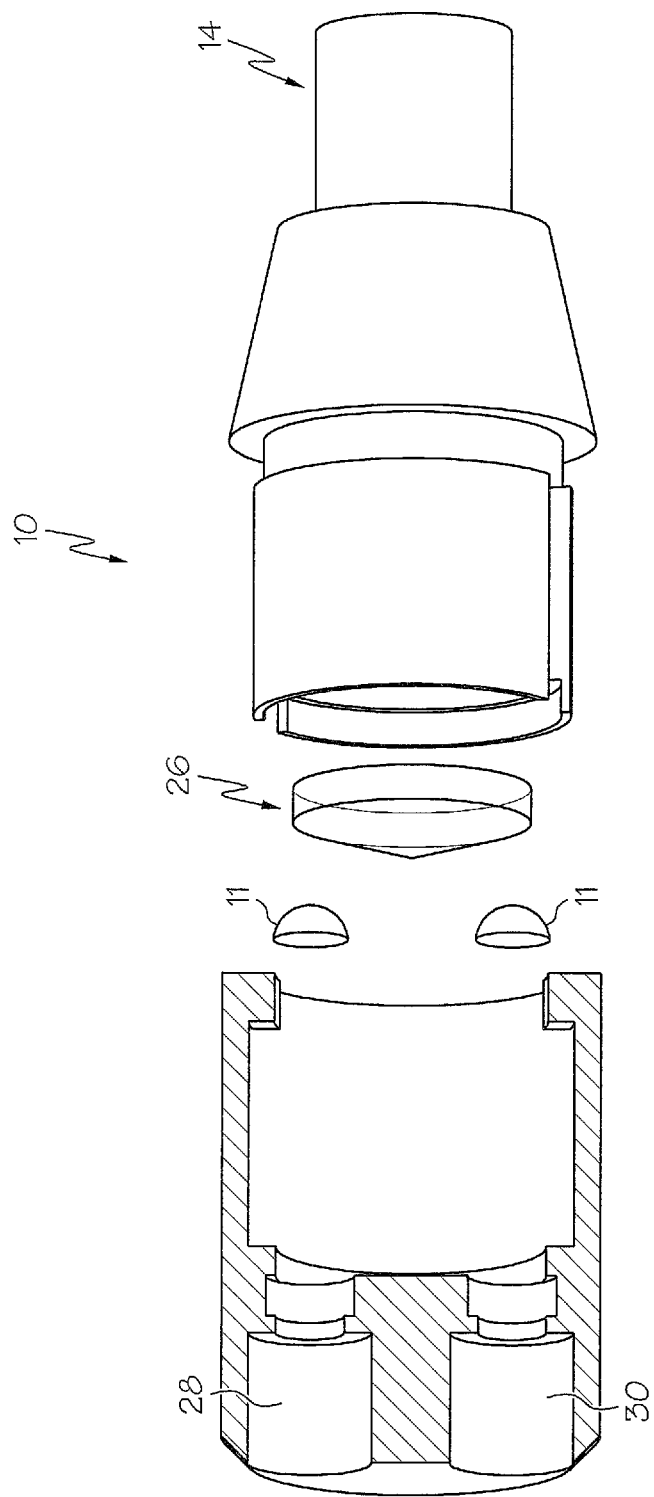

OPTICAL COUPLED SENSORS FOR HARSH ENVIRONMENTS

CROSS-REFERENCE TO RELATED APPLICATIONS

Not Applicable

STATEMENT REGARDING FEDERALLY SPONSORED RESEARCH

Not Applicable

FIELD OF THE INVENTION

This invention relates to the field of optically coupled sensors for harsh environments, namely in the high temperature environment of a hypersonic nozzle, a hypersonic flowpath, or in a high temperature combustor such as in a gas turbine or furnace.

BACKGROUND OF THE INVENTION

The hypersonic environment is extreme, involving both high temperature and oxidizing environment. In testing models in hypersonic ground facilities (or in flight), it is desirable to obtain real-time assessment of dynamic pressure and shear force (skin friction) at various places along the flow path. Furthermore, velocity profiling and flow uniformity of the hypersonic flow, at the exit plane of a hypersonic ground facility nozzle needs to be regularly assessed, preferably in real-time during testing, to better interpret external influences on test model performance.

The high speed, high temperature environment that exists in hypersonic flow applications also eliminates all non-intrusive velocity measurement techniques that rely on physical tracer particles to be propagated by the flow (such as particle image velocimetry or laser Doppler velocimetry). Multi point measurements of temperature and/or velocity using CARRS or Rayleigh molecular scattering suffer from the high cost of setup that accompanies these techniques and susceptibility to background noise/vibration, which limits their practicality towards implementation in ground test facilities.

In connection with pressure sensors, current technology in high temperature dynamic pressure sensors is limited to at most 600° C., with the need for active cooling in higher temperature situations. Active cooling is undesirable because it makes the sensors bulky and logistically challenging to integrate, while at the same time sacrificing performance.

Dynamic pressure measurements require sensing elements to be in direct contact with the fluid flow. Typically, this involves a surface with a hole aligned with the fluid flow boundary and a tube attached to the hole and leading to a pressure sensor with a diaphragm suspended in a cavity. In hot environments however, this tube is necessarily long in order to partially thermally isolate the pressure sensor. Such separation between the sensor and fluid flow creates a phase lag and signal attenuation—the tube and cavity act as a low pass filter—rendering dynamic pressure measurements problematic. While surface mounted pressure sensors do exist, they are not capable of operating at high temperatures because conversion of pressure into a signal relies on electrical circuitry that is either integrated into the sensing element, or in close proximity. Therefore, the sensor's operating envelope is restricted by the relatively low temperature capability of the electronics and electrical connections.

What is needed are optically coupled sensors that are capable of operating in ultra harsh environments, such as, the hypervelocity, high temperature, oxidizing environment of a high Mach number nozzle and the flow it produces, or the flow environment external (and internal within its flowpath) a test article flying at hypersonic speeds realizes.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

Applicant's have invented an optical sensor which can be configured for sensing pressure, shear force and/or flow velocity, the optical sensor comprising a light source; a sensor substrate, arranged to receive a force to be detected in the case of pressure and shear, the sensor substrate including an interference pattern generator, optically coupled to the light source for receiving light from the light source, and generating an interference pattern, and a detector, optically coupled to the sensor substrate for receiving the interference pattern and providing a signal which can be used to determine the force applied to the sensor substrate.

The sensor can be configured so that the light source and detector are on the same side of the sensor substrate, using a reflection grating, or the light source and detector can be on opposite sides of the sensor substrate, using slits or pinholes.

The light source can be any light source, but is preferably coherent light, such as a laser diode, and can be directly emitted onto the sensor substrate, or transmitted through a fiber optic. The light is preferred to be collimated using a collimating lens in most cases, but may not be necessary in others.

The optical sensor can be configured to detect a pressure force, which is normal to the sensor substrate, in which the sensor substrate comprises a diaphragm, with a reflection grating attached underneath the sensor diaphragm. As the pressure force causes the diaphragm to deflect from its normal unstressed position, the reflection grating flexes, which results in a change to the fringe frequency produced by the reflective grating, the change in fringe frequency allowing the determination of the pressure force applied to the diaphragm relative to the absolute pressure of the cavity underneath the sensor diaphragm and sealed from the external environment.

The optically coupled pressure sensor is configured in a hermetically sealed sensor cavity, which can be temperature monitored, as pressure is dependent on temperature, the temperature is used to calibrate the pressure measured.

In order to survive in a high temperature environment, the sensor is comprised of silicon carbide, with the sensor portion optically coupled to both the light source and detector by fiber optic, allowing the temperature sensitive portion of the device to be removed from the high temperature environment. The fiber optic can be a sapphire based fiber optic. The silicon carbide and sapphire allow the sensor to operate in temperatures of great than 1000° C., and even up to the utility temperature of silicon carbide, which is in excess of 1600° C. It should be understood that the inventive optical sensor may by used over the entire temperature range from low temperatures, at which the substrate can be made from silicon, to high temperatures, at which the substrate needs to be made from silicon carbide.

The optical sensor can be configured to detect a shear force, which is parallel to the sensor substrate, by configuring the sensor substrate as a sensor pad connected between two (or more) springs to the sensor substrate, arranged to move laterally by the shear force, and wherein the interference pattern generator is a reflection grating attached to the sensor pad, which moves laterally with the sensor pad under the shear force applied to the sensor pad, which results in a phase change as the fringe pattern moves laterally across the detector, the lateral movement of the fringe pattern allowing the determination of the shear force applied to the sensor pad.

The optical sensor can be configured for velocity profiling of the hypersonic flow (or other flow that involves compressible turbulence or thermal turbulence) by directing the light through the flow, to be detected on the opposite side of the flow using photo-detectors. Light interference at the detector aperture is generated using micro-fabricated gratings from wafer substrate material (typically silicon or silicon carbide, but can be other material as well). Velocity profiling of the hypersonic flow is accomplished by correlating optical beam steering effects at two positions in close proximity to one another so as to maintain optical aberration signature dependence and take advantage of the frozen turbulence hypothesis. The evolutionary dependence of the two signals is determined through standard cross-correlation methodology to yield the time of flight for the turbulent eddies, which are convected by the bulk flow and create the optical aberration signature. Multiplying the inverse of this result with the spatial separation of the two detectors then yields the velocity of the bulk flow. Since this is a line of sight measurement, a multi-pass, multi-axis system is needed to reconstruct tomographically the planar axial velocity field at the nozzle exit.

Therefore, the optical sensor can be configured as a velocimeter optically coupled sensor with a pair of photodetectors positioned at a predetermined distance apart, each photodetector providing a signal corresponding to the intensity of light received from the reflection grating, and a signal processor for performing cross-correlation of the two signals output from the photodetectors, to determine the time separation between the two signals, which can be used to determine the flow velocity of the fluid.

The sensor can be configured so that the light source and detector are on the same side of the sensor substrate, using a reflection grating, or the light source and detector can be on opposite sides of the sensor substrate, using slits or pinholes.

For example, the shear sensor can be configured with the light source and detector on opposite sides of the sensor substrate, with a sensor pad connected between two springs to the sensor substrate, arranged to move laterally by the shear force, and wherein the interference pattern generator is comprised of a first through-hole arranged in the stationary portion of the sensor substrate and a second through-hole arranged in the moveable sensor pad portion of the sensor substrate, wherein the change in separation distance between the moveable through-hole and the stationary through-hole creates a change in the fringe frequency of the interference pattern at the detector, which is used to determine the shear force.

The light source can be any light source, but is preferably coherent light, such as a laser diode, and can be directly emitted onto the sensor substrate, or transmitted through a fiber optic. The light is collimated using a collimating lens The detector(s) can be a photodetector, a linear detector array or an imaging device, such as a CCD or CMOS imager. The sensor substrate is preferred to be made of silicon carbide for hypersonic applications or other high temperature/harsh applications, but can be made of silicon for benign environments where temperatures are within the limits of usability of the silicon substrate.

These and other embodiments which characterize the invention are pointed out with particularity in the claims annexed hereto and forming a part hereof. However, for a better understanding of the invention, its advantages and objectives obtained by its use, reference can be made to the drawings which form a further part hereof and the accompanying descriptive matter, in which there are illustrated and described various embodiments of the invention.

BRIEF DESCRIPTION OF THE DRAWINGS

A detailed description of the invention is hereafter described with specific reference being made to the drawings.

FIG. 1 is a perspective view of an optically coupled shear or pressure sensor.

DETAILED DESCRIPTION OF THE INVENTION

Figure 2B:
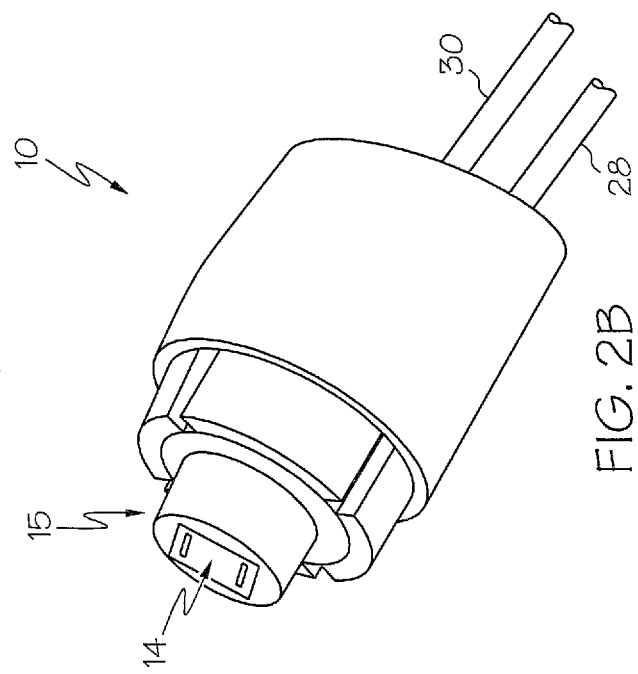
FIG. 2 is a perspective view of an optically coupled shear sensor.

While this invention may be embodied in many forms, there are described in detail herein specific embodiments of the invention. This description is an exemplification of the principles of the invention and is not intended to limit the invention to the particular embodiments illustrated.

For the purposes of this disclosure, like reference numerals in the Figures shall refer to like features unless otherwise indicated.

Referring now to FIG. 1, an embodiment of an optically coupled shear or pressure sensor is shown, at reference numeral 10. The sending optics, which produces a light, preferably coherent light, is shown at 28 and the receiving optics is shown at 30. The sending optics can be a laser diode with collimating lens 11 or an LED, and can either directly emit light or generate the light at a distance, and be optically connected to 28 via a fiber optic. The light, is directed through a focusing lens 26, through a cavity (discussed below) and to the sensor chip 14 (discussed further below).

Figure 2A:
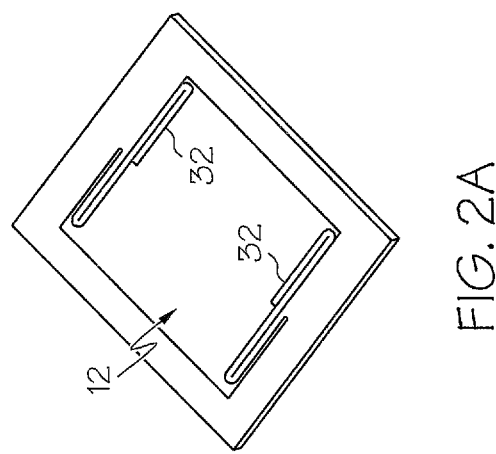

Referring now to FIG. 2, an embodiment of an optically coupled shear sensor is shown at 10. The sending fiber and receiving fiber are shown at 28 and 30. The sensing element or sensor chip is shown at 14, which is carried by the silicon carbide mounting package 15. The sensor chip 14 is shown in more detail, with the sensor pad 12 shown arranged between two springs 32, which allow the sensor pad to move latterly from side to side.

Figure 3:
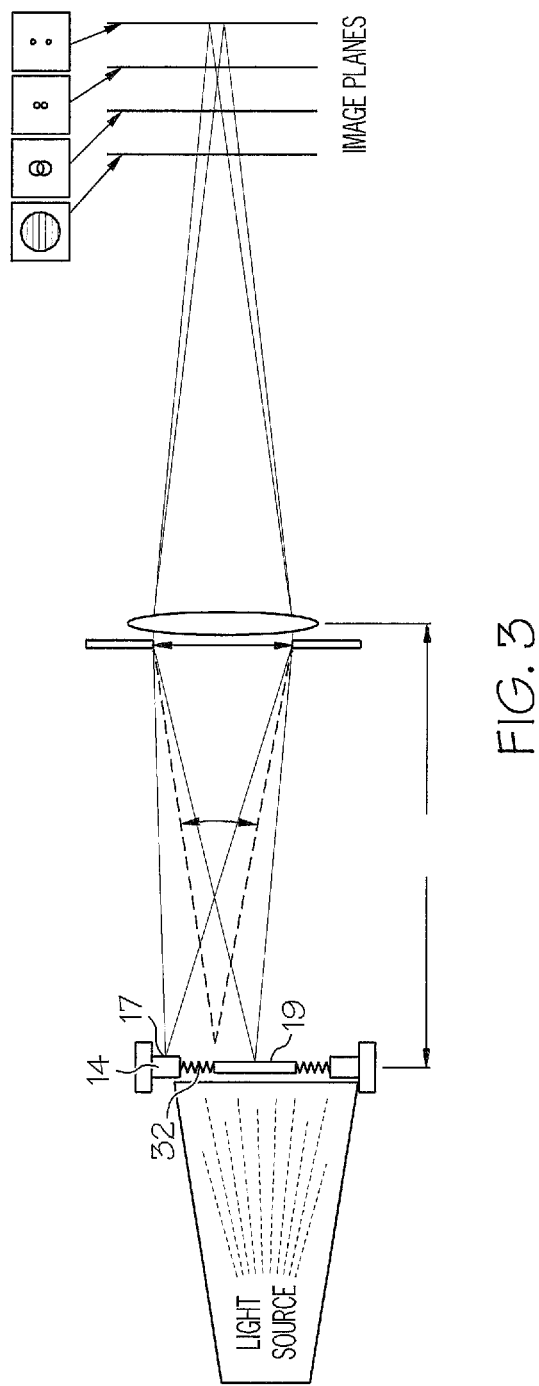
FIG. 3 is a schematic view of another embodiment of the optically coupled shear sensor in which the sending optics are arranged on the opposite side of the sensor chip than the receiving optics.

Referring now to FIG. 3, an embodiment of the shear sensor in which the sending optics are arranged on the opposite side of the sensor chip than the receiving optics is shown. In this embodiment, the stationary side of the chip substrate 14 has a pinhole or slit 17, and the movable sensor pad portion has a pinhole or slit 17. The light from the light source passes through the pinholes 17 and 19, through the aperture and imaging optics.

Figure 4:
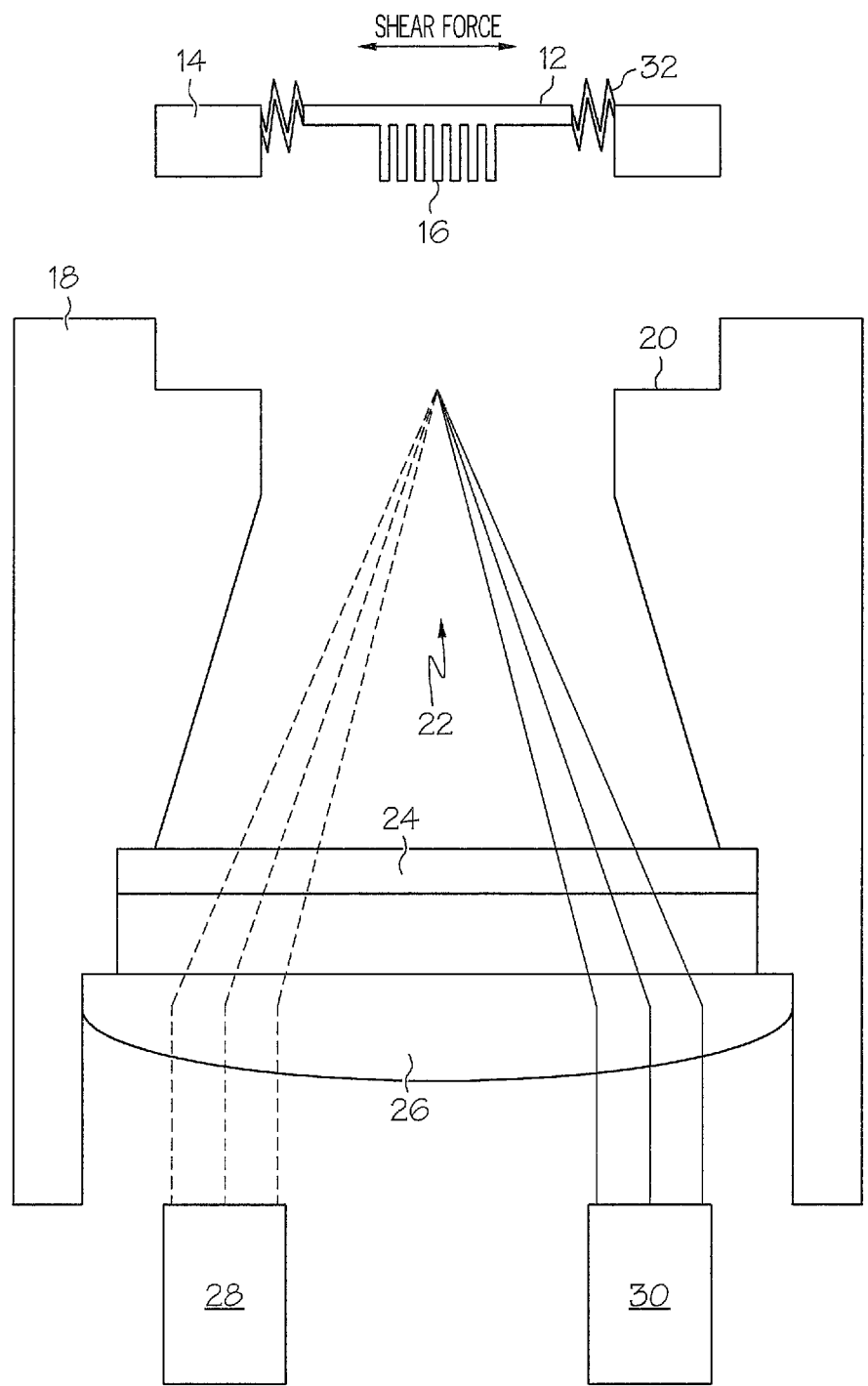
FIG. 4 is a schematic view of the optically coupled shear sensor (same side source and detector arrangement).
Figure 6:
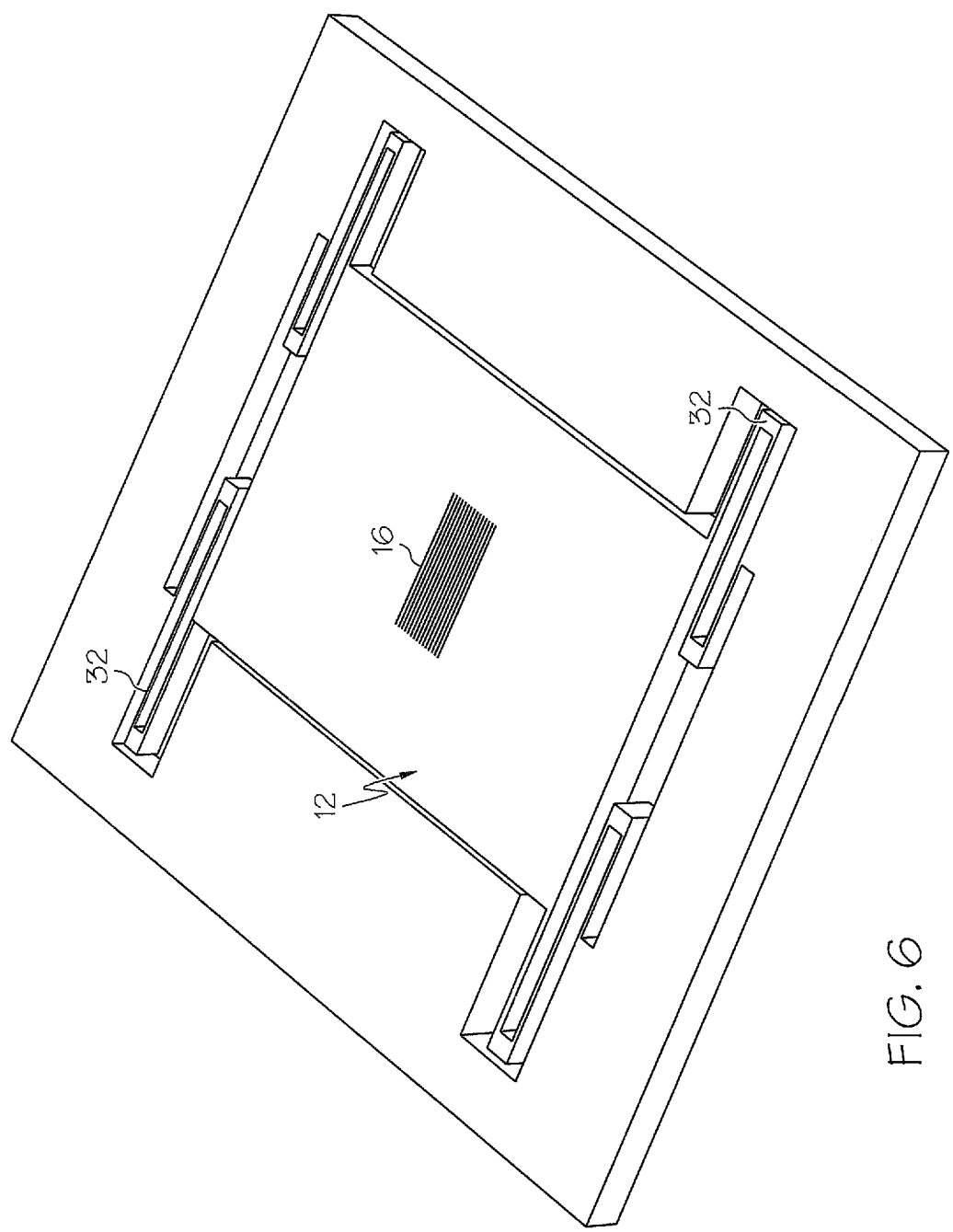
FIG. 6 is a schematic view of a typical sensor chip, sensor pad and spring arrangement utilized for the shear sensor measurement.

Referring now to FIG. 4, the sensor chip is shown at 14, which includes a sensor pad 12 connected on each side with a spring 32 (best seen in FIG. 6). Underneath the sensor pad 12, is a reflection grating 16. The sensor chip 14, sensor pad 12 and reflection grating 16 are manufactured out of silicon carbide (SiC), which has a utility temperature of in excess of 1600° C., and a melting point of 2400° C. Silicon could also be used for lower temperature applications, but not suggested for environments in excess of 300° C. to 400° C.

The sensor chip is arranged so that the flow is directed across the top portion of the sensor chip, substantially parallel to the sensor chip, as shown by the Shear Force arrows in FIG. 4.

The sensor housing 18 is provided with a bonding surface 20, to receive the sensor chip 14. The sensor housing has a cavity 22, which can optionally be hermetically sealed. A window 24 may be provided to seal the optics from the environment the sensor is exposed to. A focusing lens is shown at 26, which directs the light through the cavity 22 to the reflection grating 16. As the flow causes the sensor pad 12 to move laterally, the light generates a fringe pattern, which experiences a phase change as the fringe pattern moves laterally across the receiving optics 30 aperture, due to motion of the sensor pad.

The receiving optics 30 can be either a photo-detector, a linear detector array or an imaging device such as a CCD device. The receiving optics 30 can also be optically coupled to the detector with a fiber optic, to separate the temperature sensitive portions of the device from the sensor head portion. The fiber optic can be any conventional fiber optic capable of withstanding high temperature, or can be a sapphire fiber optic for very high temperatures, such as the 1600° C. utility temperature the sensor chip 14 can withstand. As the reflection grating moves across the focus point, it generates both a fringe lateral shift and a fringe spacing change at the detector aperture. The combined effect is either integrated by a single detector, or could be sensed by multiple detectors to get fringe motion and spacing information for a more robust measurement.

The sensor element of FIG. 4 is optically coupled to send and receive components, therefore allowing temperature sensitive components to be located away from any high temperature environment. Only the sensor element and associated package are directly exposed. Thus, temperature survivability is limited only by the material properties of sensor element and package. Given the favorable thermal mechanical properties of silicon carbide, it is anticipated that a robust microsensor system to measure dynamic pressure in high temperature environments over 1000° C. is achievable, and even in excess of 1600° C. With source and detector components located far from the high temperature environment, commercial off-the-shelf optoelectronic components can be readily utilized to give the overall sensor system robustness in terms of parts availability, which translates to lower unit and service life costs.

The sensor of FIG. 4 is a dynamic shear sensing element constructed from silicon carbide that mechanically reacts to dynamic shear force and which can be packaged in a monolithic silicon carbide pellet cast to match the geometry of the sensing element. Through the incorporation of a reflection grating on the underside of the sensing element, we can optically measure the deflection of the sensing element as it deforms under pressure using a simple interferometric-based approach. By optically coupling the sensor element to the measurement system, we avoid electrical contacts and therefore are able to enhance the thermal operating limits of the sensor by leveraging the favorable thermal mechanical properties of SiC. SiC has toughness second to diamond, and it can easily withstand temperatures in excess of 1000° C. It has a melting temperature of around 2400° C. and does not yield under pressure up to temperatures of 1600° C. Furthermore, it oxidizes very slowly at elevated temperatures.

Figure 5:
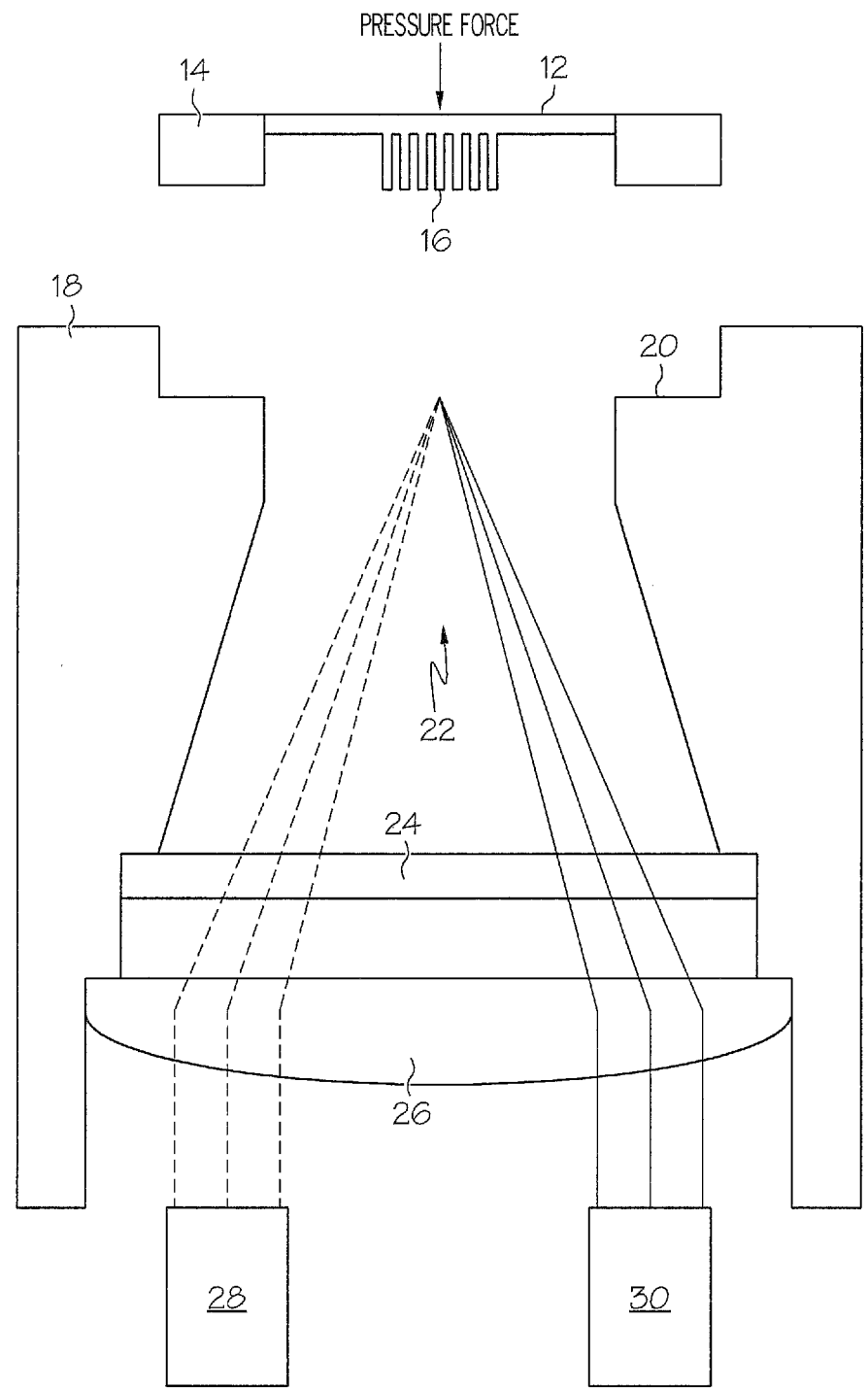
FIG. 5 is schematic view of an optically coupled pressure sensor.

Referring now to FIG. 5, a schematic embodiment of an optically coupled sensor is shown, which is configured to fit into the sensor housing of FIG. 1. The sensor chip is shown at 14, which includes a diaphragm 12. Underneath the diaphragm 12, is a reflection grating 16, which, as shown in FIG. 5, is attached directly to the bottom of the diaphragm 12. The sensor chip 14, diaphragm 12 and reflection grating 16 are manufactured out of silicon carbide (SiC), which has a utility temperature of in excess of 1600° C., and a melting point of 2400° C.

The sensor chip is arranged so that the flow is directed in a direction normal to the top portion of the sensor chip, as shown by the Pressure Force arrows in FIG. 5.

The sensor housing 18 is provided with a bonding surface 20, to receive the sensor chip 14. The sensor housing has a cavity 22, which is hermetically sealed, and a temperature sensor provides information (not shown) of the temperature in the cavity 22, which is used to calibrate the pressure measurement. A window 24 may be provided to seal the optics from the environment the sensor is exposed to. A focusing lens is shown at 26, which directs the light through the cavity 22 to the reflection grating 16. As the pressure force causes the diaphragm 12 to flex or buckle, since it is fixed at its edges, it will form a curvature. This will force the extruded elements of the linear grating to follow the curvature, and thus flare out (or in if the external pressure is less) at the tips of the reflection grating 16. A change in spacing will result in a change in the fringe frequency, which is measured at the detector, which can either be a photo-detector or linear array. This sensor measures the pressure difference (absolute in real sense) with respect to the sealed cavity. A temperature measurement of the temperature in the cavity is also needed to correct for temperature effects on the pressure measurement, as temperature is related to pressure.

Figure 7:
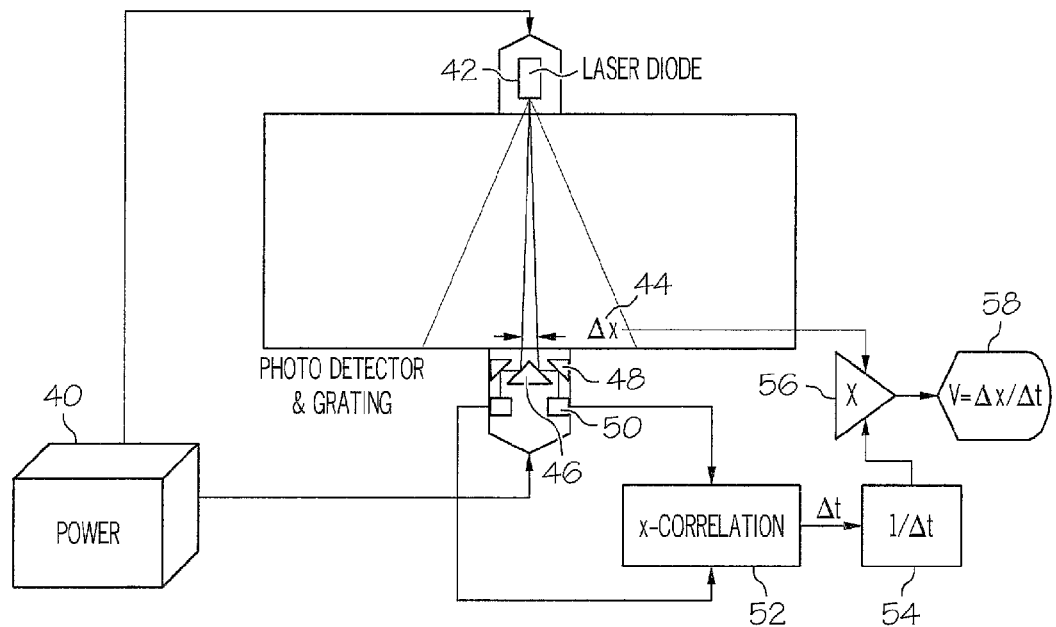
FIG. 7 is a block diagram of the optically coupled velocimeter sensor.

Referring now to FIG. 7, an embodiment of the velocity sensor in which the sending optics are arranged on the opposite side of the sensor chip than the receiving optics.

The receiving optics 30 can be either a photo-detector, a linear detector array or an imaging device such as a CCD device. The receiving optics 30 can also be optically coupled to the detector with a fiber optic, to separate the temperature sensitive portions of the device from the sensor head portion. The fiber optic can be any conventional fiber optic capable of withstanding high temperature, or can be a sapphire fiber optic for very high temperatures, such as the 1600° C. utility temperature the sensor chip 14 can withstand. As the reflection grating moves across the focus point, it generates both a fringe lateral shift and a fringe spacing change at the detector aperture. The combined effect is either integrated by a single detector, or could be sensed by multiple detectors to get fringe motion and spacing information for a more robust measurement.

The sensor element of FIG. 5 is optically coupled to send and receive components, therefore allowing temperature sensitive components to be located away from any high temperature environment. Only the sensor element and associated package are directly exposed. Thus, temperature survivability is limited only by the material properties of sensor element and package. Given the favorable thermal mechanical properties of silicon carbide, it is anticipated that a robust microsensor system to measure dynamic pressure in high temperature environments over 1000° C. is achievable, and even in excess of 1600° C. With source and detector components located far from the high temperature environment, commercial off-the-shelf optoelectronic components can be readily utilized to give the overall sensor system robustness in terms of parts availability, which translates to lower unit and service life costs.

The sensor of FIG. 5 is a dynamic pressure sensing element constructed from silicon carbide that mechanically reacts to dynamic pressure and which will be packaged in a monolithic silicon carbide pellet cast to match the geometry of the sensing element. Through the incorporation of a reflection grating on the underside of the sensing element, we can optically measure the deflection of the sensing element as it deforms under pressure using a simple interferometric-based approach. By optically coupling the sensor element to the measurement system, we avoid electrical contacts and therefore are able to enhance the thermal operating limits of the sensor by leveraging the favorable thermal mechanical properties of SiC. SiC has toughness second to diamond, and it can easily withstand temperatures in excess of 1000° C. It has a melting temperature of around 2400° C. and does not yield under pressure up to temperatures of 1600° C. Furthermore, it oxidizes very slowly at elevated temperatures.

FIG. 7 shows a block diagram for a real-time flow velocity optically coupled sensor. Power is provided at 40. The laser diode 42 emits light, which is delivered through the flow. A pair of gratings are located Delta-x apart (reference numeral 44). The splitter 46 serves to separate the light from each grating, and send it to a pair of prisms 48 and then to a pair of photo-detectors 50.

When the light goes through each grating, fringes are formed at the face of the detector. As the flow turbulence moves across the beam, index of refraction changes will bend the light so that phase changes occur at each grating that translate the fringe pattern across the detector. This causes the detector to change in intensity. The two gratings are located close to one another so as to obtain a dependency of the intensity signal detected by each detector. The separation distance is thus related to the integral time scale of the flow of interest, and needs to be selected accordingly to satisfy geometric requirements that relate to the length scales of turbulence present in the flow within the limits of the frozen turbulence hypothesis.

Figure 8:
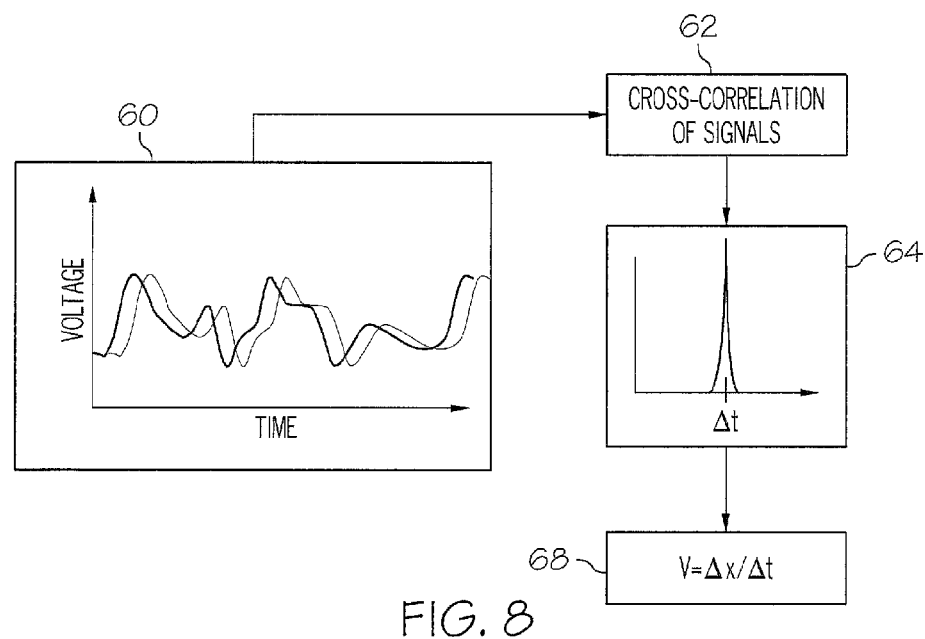
FIG. 8 is a block diagram showing the process of computing the flow velocity.

Referring now to FIG. 8, this dependency (reference numeral 60) is determined through cross-correlation of the two signals (reference numeral 62), and will yield the delta-time (reference numeral 64) needed to divide the delta-x and generate an integrated velocity signal V=Δx/Δt (reference numeral 68).

It should be understood that two separate laser diodes could be utilized, because as we are looking at dependencies in the time domain of the signal, the intensity does not have to be the same between detector signals. The grating is basically a slit pattern that is microfabricated onto a thin cover plate on top of the sensor package. Minimum of 2 slits per grating; they will allow the light to pass through and interferere on the other side.

Below this cover with the pair of slit patterns, is a beam splitter, and then a couple of prisms or mirrors to bend the light around to the detector. These latter optics are optional and just serve to make the packaging compact in some preferential way. Optionally, the light could be sent into fibers, that then terminate to detectors further away.

The important point is that this embodiment uses a pair of transmission gratings to create the interference and observe the phase change caused by index of refraction changes resulting from compressible flow turbulence or thermal turbulence. This embodiment then correlates the time-dependent signal from these gratings to determine the most probable time separation of the signals, and multiplies the inverse of this value with the spatial separation of the two gratings to determine an integrated flow velocity along the beam path. Since this is a line of sight measurement, a multi-pass, multi-axis system is needed to reconstruct tomographically the planar axial velocity field at the nozzle exit. Directional sensitivity of the velocity component is preserved by the directional alignment of the pair of slit patterns.

Figure 9:
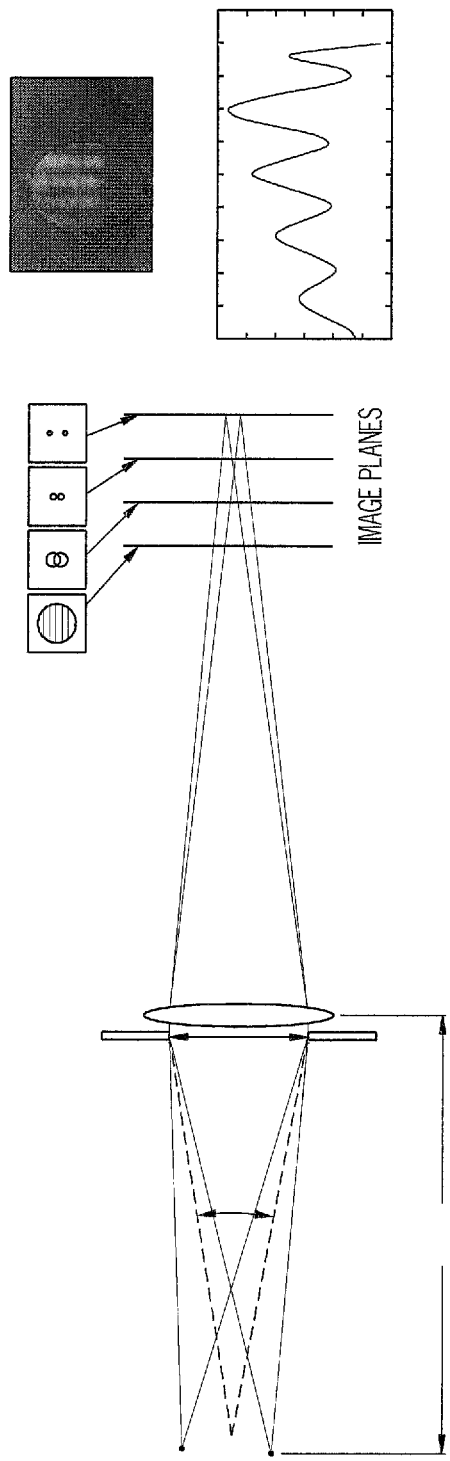
FIG. 9 is a schematic view of an alternate embodiment of the shear sensor that has the illumination source and detector separated, on opposite sides of the sensor substrate, with light transmitted through the substrate through a slits or pinholes, thus creating an interference at the plane of the detector when proper optical arrangement is made.

Referring now to FIG. 9, an alternate embodiment of the shear sensor is shown in which the sensor element is assumed to be made of a floating element that is supported to a fixed substrate via two springs. One source of light (a pinhole or slit) is located on the substrate, while another is located on the floating element (a pinhole or slit). As the floating element displaces due to flow shear, the separation distance between the two sources changes, yielding a change in the fringe frequency at the detector aperture. The change in fringe frequency can be detected through imaging optics, or at a lower fidelity using a single photodetector which simply integrates the fringe intensity to yield an analog signal out. The two methods of fringe detection have opposing requirements, in that when the imaging approach is used we want to have several fringes to work with, while when the photodetector approach is used we want to have at most 1 or 2 fringes at the aperture face. These requirements dictate the distance the aperture is placed in relation to the two sources of light.

Figure 10:
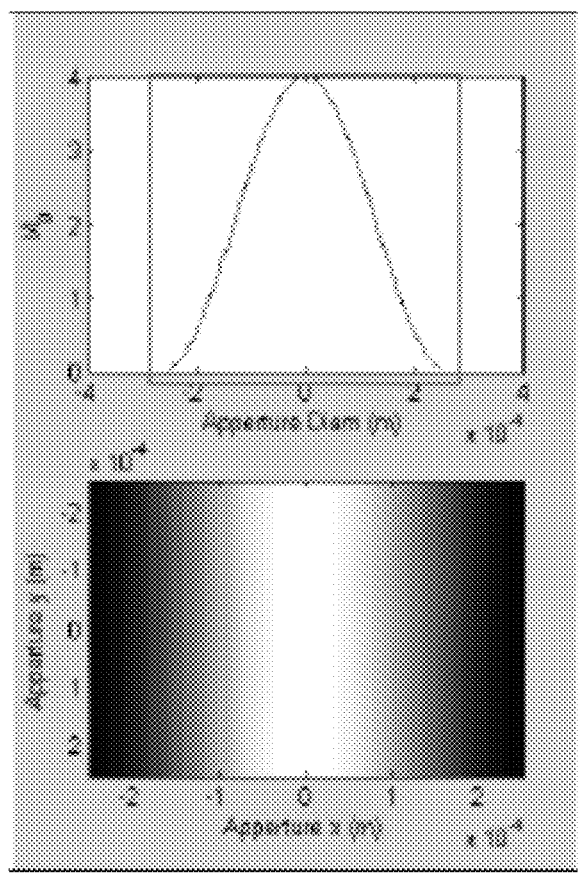
FIG. 10 is a graph showing a fringe pattern and intensity across a photodetector aperture.

Referring now to FIG. 10, a graph showing a fringe pattern and intensity across a photodetector aperture is shown. The input variables to the graph are wavelength=850 nm, photodetector aperture=0.2 $mm^2$, slit width=10 μm, slit separation=40 μm, distance from slits to aperture=25 mm and the number of slits=2. If the light intensity distribution is optimized over the detector aperture, then shift in phase will result in the movement of this distribution to the left or right. The integrated light intensity will thus vary with phase shift.

If the separation distance between the two sources remains the same, but a phase change occurs between them, then the fringe frequency remains the same but the fringe pattern displaces along the aperture. This mode of operation in regards to the measurement principle will also work in our detection scheme with the photodector, since the intensity distribution along the photodetector aperture will shift with increasing phase shift and thus result into an increase or decrease in total light intensity depending on which way the shift occurs. It should be noted that some optimization is required to assure maximum operating range of the detector without compromise in resolution.

The above disclosure is intended to be illustrative and not exhaustive. This description will suggest many variations and alternatives to one of ordinary skill in this field of art. All these alternatives and variations are intended to be included within the scope of the claims where the term "comprising" means "including, but not limited to." Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

What is claimed is:

1. An optical sensor comprising:
   a light source;
   a fixed sensor substrate, the sensor substrate including a pair of slits separated a predetermined distance apart, each slit illuminated by the light source after traveling through compressible or thermal turbulence in a fluid so as to generate an interference pattern that varies with time, the light intensity of which is converted to a pair of voltage signals by a pair of photodetectors optically aligned with the slits, and
   a signal processor for performing cross-correlation of the two voltage signals output from the photodetectors, to determine a time separation between the two voltage signals, which can be used to determine the flow velocity of the fluid.

* * * * *